(12) United States Patent
Birkenbach et al.

(10) Patent No.: US 7,463,823 B2
(45) Date of Patent: Dec. 9, 2008

(54) STEREOSCOPIC VISUALIZATION DEVICE FOR PATIENT IMAGE DATA AND VIDEO IMAGES

(75) Inventors: Rainer Birkenbach, Aufkirchen (DE); Robert Schmidt, München (DE); Richard Wohlgemuth, München (DE); Holger-Claus Roβner, Feldkirchen (DE); Nils Frielinghaus, Heimstetten (DE); Claus Schaffrath, Munich (DE); Swen Wörlein, München (DE)

(73) Assignee: BrainLAB AG, Feldkirchen (DE)

( * ) Notice: Subject to any disclaimer, the term of this patent is extended or adjusted under 35 U.S.C. 154(b) by 318 days.

(21) Appl. No.: 11/426,176

(22) Filed: Jun. 23, 2006

(65) Prior Publication Data
US 2007/0019936 A1 Jan. 25, 2007

Related U.S. Application Data

(63) Continuation-in-part of application No. 10/830,963, filed on Apr. 23, 2004, now Pat. No. 7,203,277.

(60) Provisional application No. 60/489,750, filed on Jul. 24, 2003.

(51) Int. Cl.
*G03B 29/00* (2006.01)

(52) U.S. Cl. .............................. 396/14; 348/42; 348/47; 348/51; 359/467

(58) Field of Classification Search ................... 396/14; 345/9, 156, 418, 630, 5, 6; 600/421, 425, 600/426, 427, 429; 348/42, 47, 51, 53; 359/467
See application file for complete search history.

(56) References Cited

U.S. PATENT DOCUMENTS

| 5,526,812 | A | * | 6/1996 | Dumoulin et al. | 600/407 |
| 5,694,142 | A | | 12/1997 | Dumoulin et al. | 345/9 |
| 5,715,836 | A | | 2/1998 | Kliegis et al. | 600/425 |
| 5,765,561 | A | | 6/1998 | Chen et al. | 600/407 |
| 5,961,456 | A | * | 10/1999 | Gildenberg | 600/429 |
| 5,978,143 | A | * | 11/1999 | Spruck | 359/619 |
| 6,038,467 | A | | 3/2000 | De Bliek et al. | 600/424 |
| 6,414,708 | B1 | * | 7/2002 | Carmeli et al. | 348/42 |
| 6,477,400 | B1 | | 11/2002 | Barrick | 600/426 |
| 6,490,467 | B1 | | 12/2002 | Bucholz et al. | 600/411 |
| 6,640,128 | B2 | | 10/2003 | Vilsmeier et al. | 600/427 |

(Continued)

FOREIGN PATENT DOCUMENTS

EP 0 672 389 A2 9/1995

(Continued)

*Primary Examiner*—W. B. Perkey
*Assistant Examiner*—Warren K Fenwick
(74) *Attorney, Agent, or Firm*—Renner, Otto, Boisselle & Sklar, LLP

(57) ABSTRACT

A system for visually combining patient image data from transillumination and/or tomographic imaging methods and/or object image data with video images includes an image display device having an auto-stereoscopic monitor, at least one camera and a computer-assisted navigation system. The navigation system is operable to detect spatial positions of a part of the patient's body via a first tracking device attached to the body, and spatial positions of said image display device and/or said at least one camera via a second tracking device attached to the image display device or the camera, wherein the image display device and the at least one camera are assigned to each other and are formed as a portable unit.

13 Claims, 3 Drawing Sheets

U.S. PATENT DOCUMENTS

| | | | |
|---|---|---|---|
| 6,644,852 B2 | 11/2003 | Crain et al. | 378/197 |
| 7,050,845 B2 | 5/2006 | Vilsmeier | 600/427 |
| 7,084,838 B2 * | 8/2006 | Yoon | 345/6 |
| 2001/0035871 A1 | 11/2001 | Bieger et al. | 345/630 |
| 2002/0082498 A1 | 6/2002 | Wendt et al. | 600/411 |
| 2002/0140694 A1 * | 10/2002 | Sauer et al. | 345/419 |
| 2002/0163499 A1 * | 11/2002 | Sauer | 345/156 |
| 2005/0020909 A1 | 1/2005 | Moctezuma de la Barrera et al. | 600/424 |

FOREIGN PATENT DOCUMENTS

| | | |
|---|---|---|
| EP | 0 877 274 | 11/1998 |
| EP | 1 321 105 | 6/2003 |
| WO | 96/20421 A | 7/1996 |
| WO | 00/36845 | 6/2000 |
| WO | 03/002011 | 1/2003 |

* cited by examiner

STEREOSCOPIC VISUALIZATION DEVICE FOR PATIENT IMAGE DATA AND VIDEO IMAGES

RELATED APPLICATION DATA

This application is a continuation-in-part of U.S. Non-Provisional application Ser. No. 10/830,963 filed on Apr. 23, 2004 now U.S. Pat. No. 7,203,277, which claims priority to U.S. Provisional Application No. 60/489,750 filed on Jul. 24, 2003, both of which are incorporated herein by reference in their entirety.

FIELD OF THE INVENTION

The present invention relates to medical video imaging and, more particularly, to a portable device for visually combining patient image data from transillumination and/or tomographic imaging methods and/or object image data with video images.

BACKGROUND OF THE INVENTION

EP 1 321 105 B1 discloses a portable screen-camera unit that includes a camera mounted on a rear side of a screen. A physician can hold the portable screen together with the corresponding camera in front of a patient (e.g., in front of a particular body part). By displaying in combination patient image data from transillumination and/or tomographic imaging methods as well as video images, the physician can view the exterior area of the patient's body part and can simultaneously obtain superimposed images of interior structures of the patient's body part.

A disadvantage of this portable screen-camera unit is that the physician and/or any observer is only provided with a flat projection, i.e., a two-dimensional view. Depth information is difficult to estimate or infer from the unit.

SUMMARY OF THE INVENTION

A device for displaying images includes an image display device, a camera device and a computer-assisted navigation system. The navigation system can detect a spatial position of the image display device and/or the camera device as well as the spatial position of a patient's body part via tracking means attached thereto.

Two-dimensional representations of the image display device can be extended to a three-dimensional representation, wherein the image display device utilizes the fact that the patient image data are in many cases already available as spatial and three-dimensional data (e.g., as image data that originate from transillumination and/or tomographic imaging methods). If, for example, a CT recording is obtained, three-dimensional or spatial patient image data are available from the tomographs. In conventional screen-camera units, this fact has only been utilized to the extent that it has been possible to display the structural features of the body part correctly projected in the viewing direction, though only in two-dimensions on the screen.

It is possible to visually provide the entire informational content of the three-dimensional patient image data sets. To this end, an auto-stereoscopic monitor can be used that provides the observer with a three-dimensional image, without requiring additional aids such as special spectacles, for example. The auto-stereoscopic monitor can be provided with the patient image data in a suitable way, such that the patient image data appear three-dimensional to the observer.

If the camera means is a stereoscopic camera means, the data captured by the camera means of the patient's exterior also can be manipulated such that the monitor, provided with said data, generates a stereoscopic and/or three-dimensional video image of the patient's body part. Because the data can be positionally assigned by means of the navigation system, the two images can be superimposed such that a three-dimensional view is created on the monitor, which allows the observer to simultaneously observe the patient's body part by way of exterior and interior features and, thus, to also obtain depth information.

Auto-stereoscopic monitors are available and can be adapted to the requirements of the application. There are so-called parallax displays that are based on a two-dimensional image plane, wherein diffuse light can be actively focused and aligned. So-called parallax barrier systems use a kind of aperture mask, e.g., an opaque layer in front of the image surface that is interrupted by regular slits, wherein a defined image region can be presented depending on the angle of view. Other systems also can be used with the present invention, including lens-based systems in which the views are separated before the screen by lens elements. Round lenses can be used (full parallax) or semi-cylindrical optical lenses that use sub-pixel control (slanted lenticular sheets) provide improved resolution when aligned obliquely. Further, oblique sub-pixel arrays avoid moiré effects and black transitions. It is also possible to use alternative parallax systems, e.g. prism systems or polarizing filters.

The camera means can include a single camera. In one embodiment, the camera means includes at least two cameras that are arranged on a rear or back side of the image display device (e.g., on the opposite side to the screen) and wherein a distance between the two cameras can be adjusted to a predetermined distance range between the observer and the monitor. The camera means also can include movable cameras. The movable cameras enable one to set an intersecting region of the fields of vision of the cameras in accordance with the distance between the cameras and the object observed and/or in accordance with the distance between the observer and the monitor. Thus, the entire array, as well as the software, can be set to a typical scenario prior to use, wherein corresponding predetermined fixed values or ranges of values can be used. In this way, for example, image rendering can be simplified and quickly calculated. Further, the movable cameras increase flexibility with respect to the distance between the portable image display device and the patient.

The monitor can be controlled by an image processing unit that spatially assigns and combines the stereoscopic video images and three-dimensionally calculated patient body structures from the transillumination images and/or tomographs, generating a combined stereo image. As already indicated above, the monitor can be an aperture mask or lens monitor having one or more stereo observation zones, e.g., single-user and multi-user configurations can be used. In accordance with one embodiment, one or more observation zones can be arranged stationary relative to the monitor, e.g., a so-called passive system can be provided wherein the observer views a clear stereoscopic image when he is standing in front of the monitor in one or more predetermined observation zones.

Further, an observer tracking unit can be assigned to the monitor to create a so-called active system that tracks the observation zone(s) of the observer. The image processing unit can display an image on the monitor that develops its observation zone(s) at each observer location or at each tracked observer location. Such an "active" system that monitors a location of the observer provides the observer with the best stereoscopic image at the observer's location.

The observer tracking unit can be a tracking unit of the navigation system or can be directly assigned to the navigation system. In another embodiment, the observer tracking unit can be a video tracking unit with a separate video camera that identifies and tracks the position of the head or the eyes of the observer by means of image recognition.

It is possible to use the image processing unit of the navigation system as the image processing unit, or an image processing unit that is directly assigned to the navigation system, e.g. an image processing unit in the portable screen unit tracked by the navigation system. Image processing also can be performed separately by a separate image processing unit, the data then being transferred via a wired or wireless link to the monitor.

In accordance with another embodiment, the device also includes a user input device, by means of which the user can toggle between a stereoscopic and normal image observation mode. Also, the user can toggle between displaying one or more observation zones. The device also can include inputs for enabling image-assisted treatment or treatment planning, and for controlling the movable cameras.

In the following, the invention is explained in more detail on the basis of an embodiment, wherein reference is made to the enclosed figures. The invention can be implemented with any of its described features, individually or in combination, and also includes the procedural embodiment of the features described on the basis of the device.

DETAILED DESCRIPTION

Figure 1:
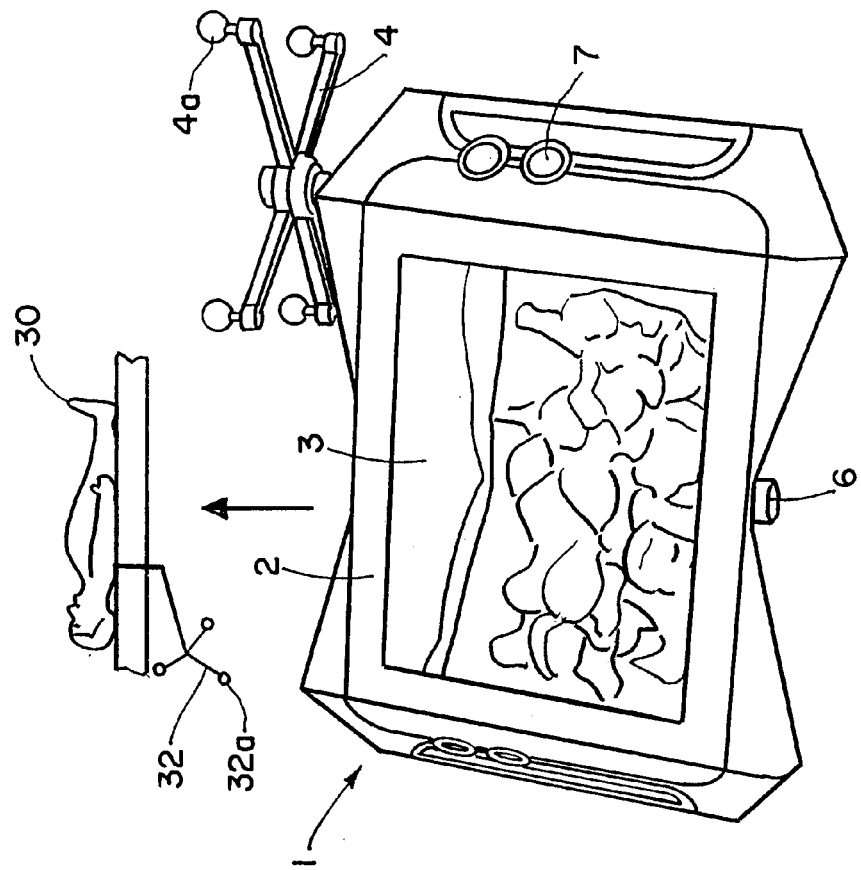
FIG. 1 illustrates a front view of an exemplary screen-camera unit and navigation system in accordance with the invention.
Figure 1:
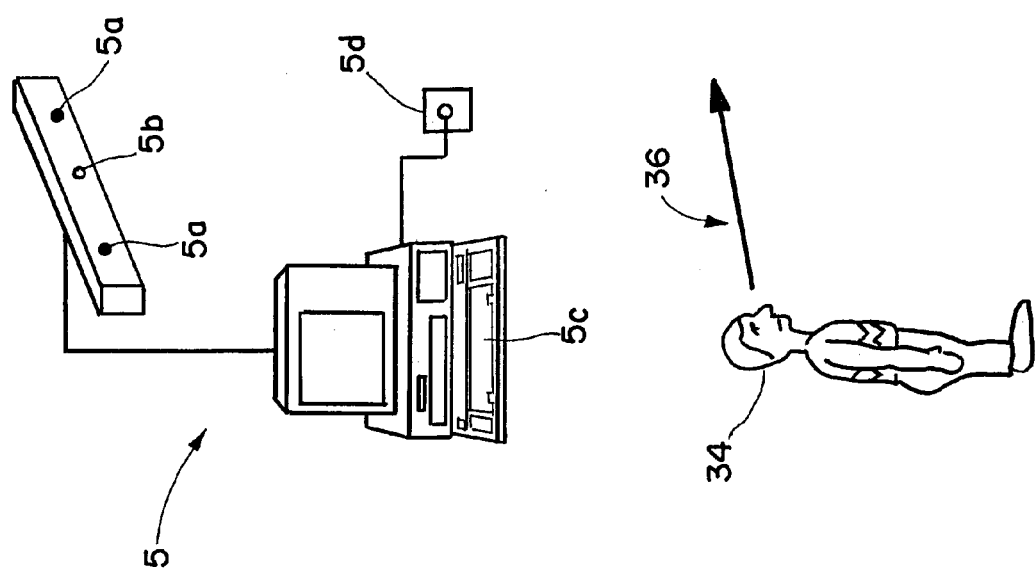

Referring to FIG. 1, an image display unit 1 is shown in a perspective view from the front. The image display unit includes a casing 2, which is fitted on a front side with a screen 3. The screen 3 is an auto-stereoscopic screen or monitor, and in the present case a partially covered patient's back is shown on its display with the spinal column beneath.

Figure 2:
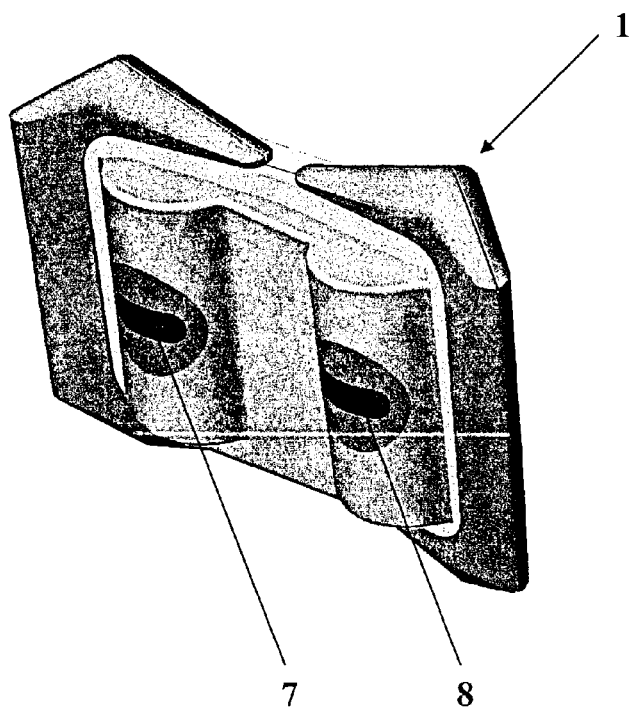
FIG. 2 illustrate a rear view of an exemplary screen-camera unit including two rear-side cameras.
Figure 3:
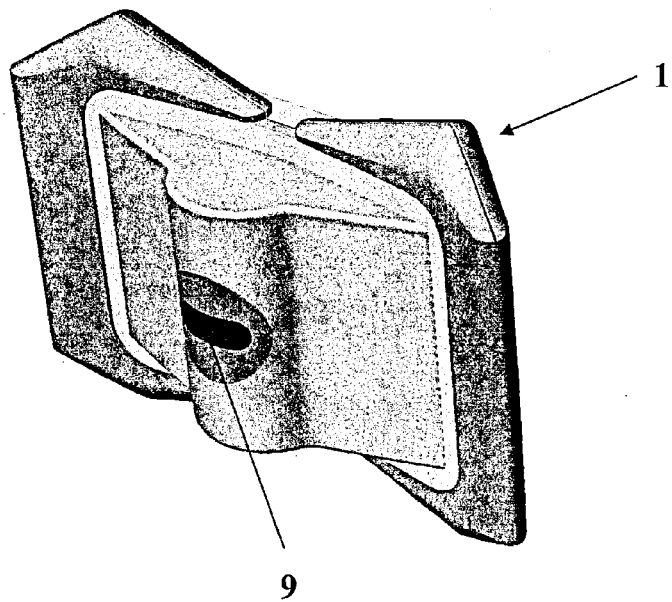
FIG. 3 illustrate a rear view of an exemplary screen-camera unit including one rear-side camera.

A reference star 4 with markers 4a is shown on top of the casing 2 and enables a position of the image display unit 1 in a localizing space of a navigation system 5 to be established. Thus, a position of the cameras 7 and 8 (shown in FIG. 2 on the rear side of the image display unit 1) also can be established in the navigation system's localizing space. More particularly, since the patient 30 is also tracked by the navigation system 5 via reference star 32 with markers 32a, the video image of the cameras 7 and 8 also can be spatially assigned in the navigation system 5 and displayed in the correct spatial positional relationship to the interior patient structures.

Since the two cameras 7 and 8 are capable of generating a stereoscopic image and the screen 3 is an auto-stereoscopic screen, and since the data on the interior patient structure (e.g., the spinal column) are additionally provided as spatial data (e.g. from a CT recording), all the image information can be reproduced in a single combined and superimposed stereo image, such that an image depth effect is created for the observer 34. In the present case, the tracking means (e.g., the reference stars 4 and 32 and markers 4a and 32a) is an optical tracking means for the navigation system 5. The navigation system 5 includes, for example, two spaced infrared cameras 5a and an infrared light emitter 5b. The navigation system 5 also include a computational unit 5c, such as a computer or the like. Other navigation and/or tracking systems (magnetic or actively emitting marker or reference arrays) also can be used without departing from the scope of the invention. Additionally, the navigation system 5, via integral or separate cameras 5d, also may operate as an observer tracking unit that can track observation zones 36 of an observer 34.

The observer 34 can view a three-dimensional representation of the patient 30 and look into the patient, so to speak, such that a stereo image or three-dimensional image of a "glass patient" is created.

A fixing device 6 also is attached to the image display unit 1 in a lower part of the casing 2, for example. With the aid of the fixing device 6, the image display unit 1, which is embodied as a portable unit, can be temporarily fixed to a mounting (not shown) if the intention is to view onto/into the patient from the same direction over a longer period of time. Furthermore, the screen 3 also includes input buttons 7, one of which is shown on the right of the casing 2. With the aid of the input buttons 7 (a touch screen or other input device also can be used), it is possible to toggle between a stereoscopic and normal image observation mode, for example. Furthermore, it is possible to toggle between displaying with one or more observation zones 36, and/or enabling inputs for image-assisted treatment or treatment planning. If the cameras 7 and 8 are formed on the rear side as movable cameras to enable a range of field of vision to be set or adjusted, the movement of the cameras 7 and 8 also can be controlled with the aid of the input buttons 7. Preferably, a menu control is provided that can be accessed via the buttons 7.

Figure 4:
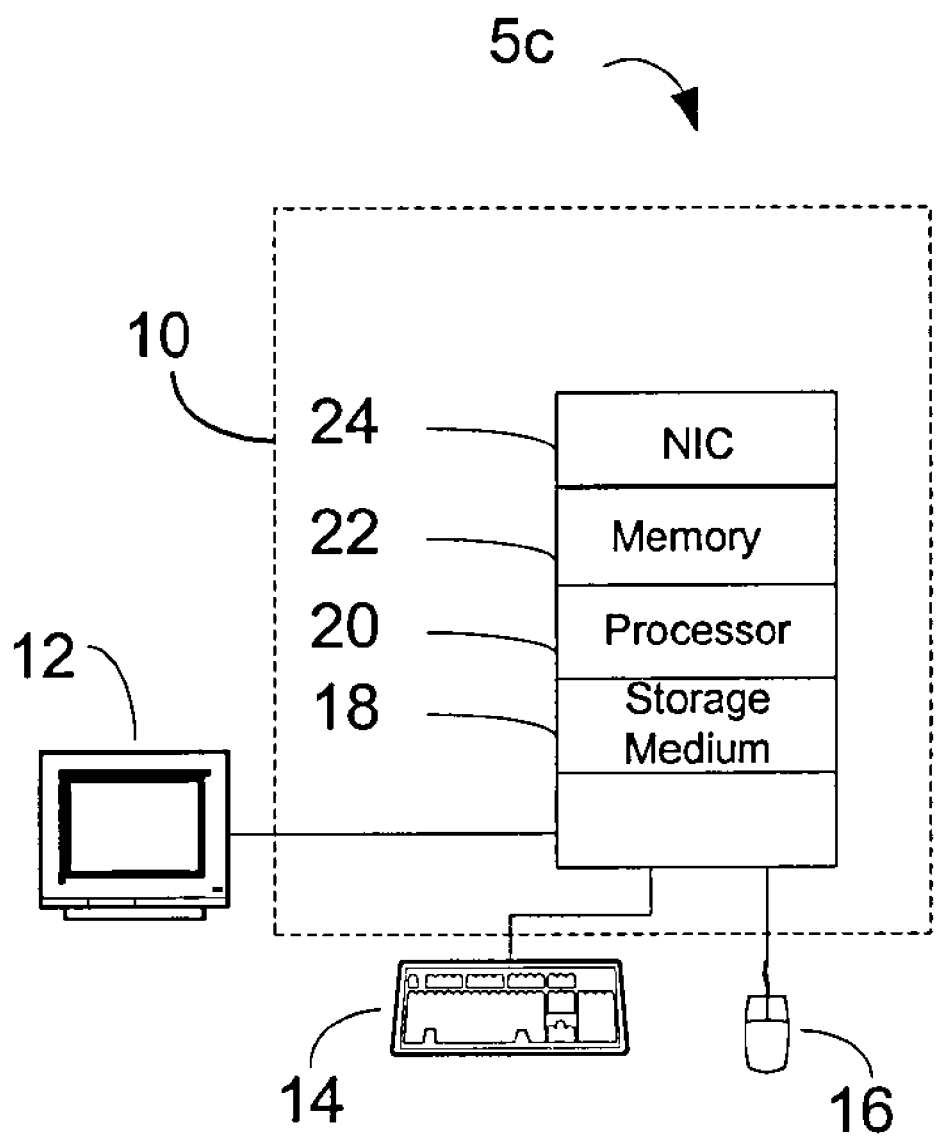
FIG. 4 is a block diagram of an exemplary computational unit that can be used to implement the method of the present invention.

Moving to FIG. 4, the computational unit 5c of the navigation system 5 is illustrated in block diagram form. The computational unit 5c includes a computer 10 for processing data, and a display 12 (e.g., a Cathode Ray Tube, Liquid Crystal Display, or the like) for viewing system information. A keyboard 14 and pointing device 16 may be used for data entry, data display, screen navigation, etc. The keyboard 14 and pointing device 16 may be separate from the computer 10 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 14 and pointing device 16. Touch screens may be beneficial when the available space for a keyboard 14 and/or a pointing device 16 is limited.

Included in the computer 10 is a storage medium 18 for storing information, such as application data, screen information, programs, etc. The storage medium 18 may be a hard drive, an optical drive, or the like. A processor 20, such as an AMD Athlon 64™ processor or an Intel Pentium IV® processor, combined with a memory 22 and the storage medium 18 execute programs to perform various functions, such as data entry, numerical calculations, screen display, system setup, etc. The processor 20 also may operate as an image processing unit, for example, so as to process graphical data for display on image display unit 1 and/or display 12. A network interface card (NIC) 24 allows the computer 10 to communicate with devices external to the computational unit 5c.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A system for visually combining patient image data from transillumination and/or tomographic imaging methods and/or object image data with video images, comprising:
    an image display device including an auto-stereoscopic monitor;
    at least one camera; and
    a computer-assisted navigation system operable to detect spatial positions of a part of the patient's body via a first tracking device attached to the body, and spatial positions of said image display device and/or said at least one camera via a second tracking device attached to the image display device and/or the camera, wherein the image display device and the at least one camera are assigned to each other and are formed as a portable unit.

2. The device as set forth in claim 1, wherein the at least one camera is a stereoscopic camera.

3. The device as set forth in claim 1, wherein the at least one camera comprises at least two cameras arranged on a side opposite to the auto-stereoscopic monitor, and a distance between the at least two cameras is adjustable to a predetermined distance or range between an observer and the auto-stereoscopic monitor.

4. The device as set forth in claim 3, wherein the cameras are arranged on a rear side of the image display device.

5. The device as set forth in claim 3, wherein the cameras comprise movable cameras configured to set an intersecting region of the fields of vision of the cameras in accordance with the distance between the cameras and the object observed and/or in accordance with the distance between the observer and the auto-stereoscopic monitor.

6. The device as set forth in claim 1, wherein the auto-stereoscopic monitor is controlled by an image processing unit that spatially assigns and combines stereoscopic video images and three-dimensionally calculated patient body structures from the transillumination images and/or tomographs such that a combined stereo image is displayed.

7. The device as set forth in claim 1, wherein the auto-stereoscopic monitor is an aperture mask or lens monitor having one or more stereo observation zones.

8. The device as set forth in claim 7, wherein the observation zone(s) are arranged stationary relative to the auto-stereoscopic monitor.

9. The device as set forth in claim 7, further comprising an observer tracking unit assigned to the auto-stereoscopic monitor, wherein an image processing unit tracks the observation zone(s) to an observer by displaying an image on the auto-stereoscopic monitor that develops its observation zone(s) at each observer location or at each tracked observer location.

10. The device as set forth in claim 9, wherein the observer tracking unit is a tracking unit of the navigation system or is directly assigned to the navigation system.

11. The device as set forth in claim 9, wherein the observer tracking unit is a video tracking unit with a separate video camera that identifies and tracks the position of the head or the eyes of the observer by image recognition.

12. The device as set forth in claim 9, wherein the image processing unit is the image processing unit of the navigation system or is directly assigned to the navigation system.

13. The device as set forth in claim 1, further comprising a user input device configured to enable at least one of toggling between a stereoscopic and normal observation mode, toggling between displaying one or more observation zones, controlling at least one movable camera, and enabling image assisted treatment or treatment planning.

* * * * *